United States Patent
Huang et al.

(10) Patent No.: US 9,877,655 B2
(45) Date of Patent: Jan. 30, 2018

(54) DIAGNOSTIC INSTRUMENT AND METHOD

(71) Applicant: National University of Singapore, Singapore (SG)

(72) Inventors: Zhiwei Huang, Singapore (SG); Mads Sylvest Bergholt, Singapore (SG); Wei Zheng, Singapore (SG); Khek Yu Ho, Singapore (SG)

(73) Assignee: NATIONAL UNIVERSITY OF SINGAPORE, Singapore (SG)

( * ) Notice: Subject to any disclaimer, the term of this patent is extended or adjusted under 35 U.S.C. 154(b) by 28 days.

(21) Appl. No.: 14/768,521

(22) PCT Filed: Feb. 19, 2014

(86) PCT No.: PCT/SG2014/000063
§ 371 (c)(1),
(2) Date: Aug. 18, 2015

(87) PCT Pub. No.: WO2014/129970
PCT Pub. Date: Aug. 28, 2014

(65) Prior Publication Data
US 2016/0000330 A1    Jan. 7, 2016

(30) Foreign Application Priority Data
Feb. 19, 2013 (GB) .................... 1302886.5

(51) Int. Cl.
*A61B 5/00* (2006.01)
*G01J 3/28* (2006.01)
(Continued)

(52) U.S. Cl.
CPC ........ *A61B 5/0075* (2013.01); *A61B 1/00165* (2013.01); *A61B 5/0084* (2013.01);
(Continued)

(58) Field of Classification Search
CPC . A61B 5/0075; A61B 5/00165; A61B 5/0084; G01J 3/0218; G01J 3/0272;
(Continued)

(56) References Cited

U.S. PATENT DOCUMENTS 5,223,715 A * 6/1993 Taylor .................. G01N 21/255
                                              250/339.02
5,559,597 A * 9/1996 Battey ...................... G01J 3/02
                                                   356/328
(Continued)

FOREIGN PATENT DOCUMENTS

| CN | 102725624 A | 10/2012 |
|---|---|---|
| WO | 2010140998 A1 | 12/2010 |
| WO | 2013103475 A2 | 7/2013 |

OTHER PUBLICATIONS

Second Office Action dated Mar. 1, 2017 in corresponding Chinese Patent Application No. 2014800091259.
(Continued)

*Primary Examiner* — Catherine Voorhees
(74) *Attorney, Agent, or Firm* — Ming Chow; Sinorica, LLC

(57) ABSTRACT

A diagnostic instrument comprises a monochromatic light source, transmission means to transmit light from the light source to a test site, collection means to transmit scattered light from the test site, and spectral analysis apparatus to receive light from the collection means, the spectral analysis apparatus comprising a diffraction grating having a first grating element and a second grating element, wherein the first grating element diffracts light within a first wavelength range and the second grating element diffracts light within a second wavelength range, the spectral analysis apparatus further comprising a light-sensing apparatus, the first grating element arranged to diffract light onto a first area of the light-sensing apparatus and the second grating element
(Continued)

arranged to diffract light onto a second area of the light-sensing apparatus.

8 Claims, 8 Drawing Sheets

(51) Int. Cl.
    *G01J 3/44*     (2006.01)
    *G01N 21/65*     (2006.01)
    *G02B 23/24*     (2006.01)
    *G02B 23/26*     (2006.01)
    *G01J 3/02*     (2006.01)
    *A61B 1/00*     (2006.01)
    *G01J 3/18*     (2006.01)

(52) U.S. Cl.
    CPC ........... *G01J 3/0218* (2013.01); *G01J 3/0272* (2013.01); *G01J 3/18* (2013.01); *G01J 3/28* (2013.01); *G01J 3/44* (2013.01); *G01N 21/65* (2013.01); *G02B 23/2469* (2013.01); *G02B 23/26* (2013.01); *G01N 2201/129* (2013.01)

(58) Field of Classification Search
    CPC ...... G01J 3/18; G01J 3/28; G01J 3/44; G01N 21/65; G01N 2201/129; G02B 23/26; G02B 23/2469
See application file for complete search history.

(56) References Cited

U.S. PATENT DOCUMENTS

| | | | |
|---|---|---|---|
| 6,486,948 B1 | 11/2002 | Zeng | |
| 2005/0010130 A1* | 1/2005 | Morris | A61B 5/0059 600/562 |
| 2006/0139633 A1 | 6/2006 | Puppels et al. | |
| 2009/0066934 A1* | 3/2009 | Gao | G01N 15/1463 356/73 |
| 2010/0208258 A1* | 8/2010 | Shibayama | G01J 3/02 356/326 |
| 2012/0259229 A1 | 10/2012 | Wang et al. | |

OTHER PUBLICATIONS

Supplementary European Search Report, EP 14754054, dated Nov. 15, 2016.

\* cited by examiner

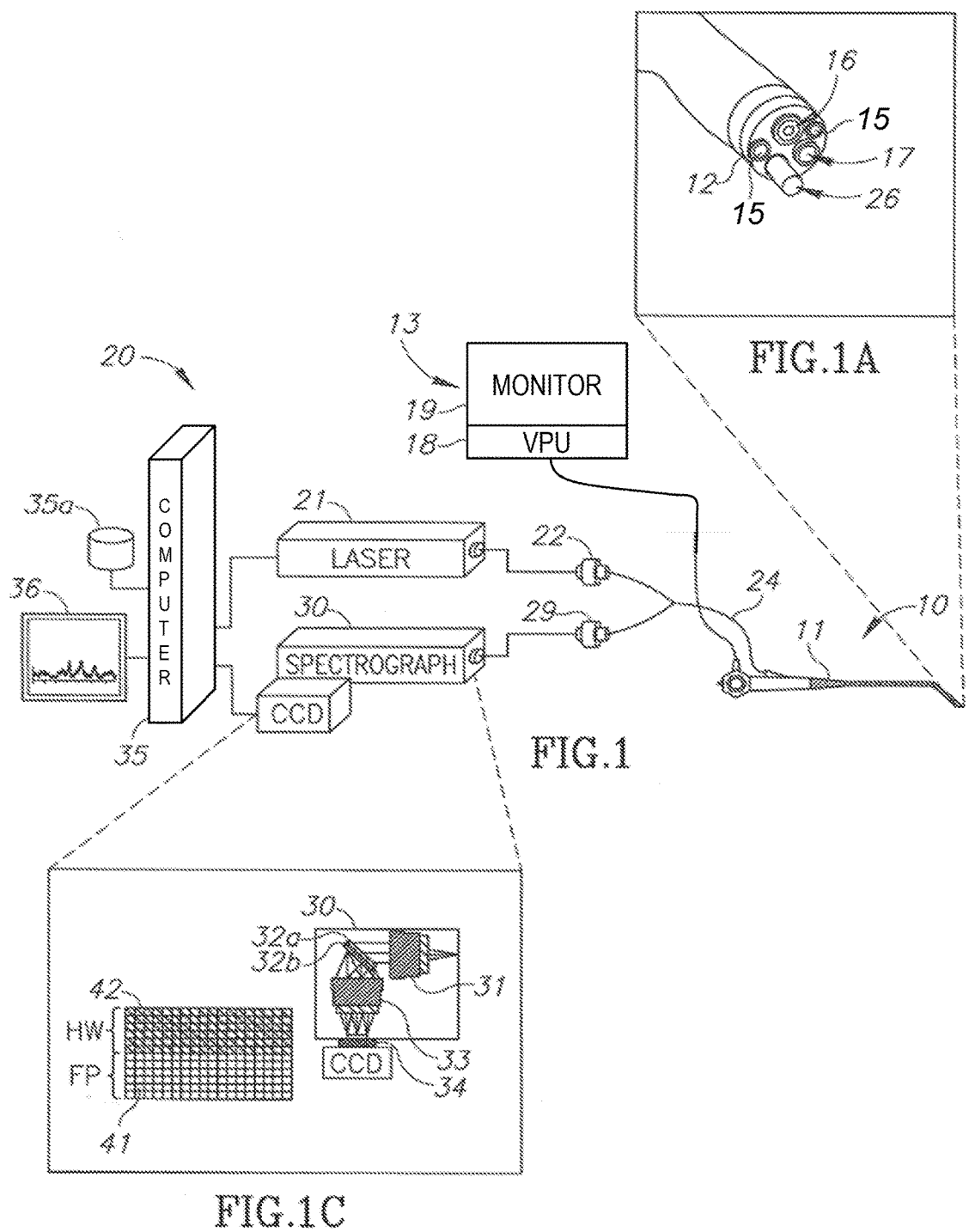

DIAGNOSTIC INSTRUMENT AND METHOD

This is a National Phase Application filed under 35 U.S.C. 371 as a national stage of PCT/SG2014/000063, filed Feb. 19, 2014, an application claiming the benefit of Great Britain Application No. 1302886.5, filed Feb. 19, 2013, the content of each of which is hereby incorporated by reference in its entirety.

The present invention relates to a diagnostic apparatus and method for using Raman spectroscopy for real-time in vivo tissue measurements, particularly but not exclusively for use in an endoscope.

BACKGROUND TO THE INVENTION

Raman spectroscopy is a technique which uses inelastic or Raman scattering of monochromatic light. Conventionally, the monochromatic light source is a laser in the visible or near infrared ("NIR") range. The energy of the scattered photons is shifted up or down in response to interaction with vibrational modes or excitations in the illuminated material, varying the wavelength of the scattered photons. Accordingly, the spectra from the scattered light can provide information about the scattering material.

It is known to use NIR Raman spectroscopy as a potential technique for characterisation and diagnosis of precancerous and cancerous cells in vivo in a number of organs. The technique is desirable as it can be non-invasive or minimally invasive, not requiring biopsies or the other removal of tissue. It is known to use NIR Raman spectroscopy in two wavelength ranges. The first is the so-called fingerprint ("FP") range, with wave numbers from 800 to 1800 $cm^{-1}$, owing to the wealth of highly specific bimolecular information, for example from protein, DNA and lipid contents, contained in this spectral region for tissue characterisation and diagnosis. The disadvantage of this wavelength range is, that when used with a commonly used 785 nm laser source, the illuminated tissue autofluoresces, generating a strong background signal. Further, where the probe uses optical fiber links, a Raman signal is scattered from the fused silica in the optical fibers. In particular, where a charge-coupled device ("CCD") is used to measure the scattered spectra, the autofluorescent signal can saturate the CCD and interfere with the detection of the comparatively weak Raman signals in this wavelength area.

It is also known to measure Raman scattering in a relatively high wavenumber range ("HW") with wavenumbers in the range 2800 to 3700 $cm^{-1}$. This wavenumber range is desirable as strong Raman signals are generated from $CH_2$ and $CH_3$ moiety stretching vibrations in proteins and lipids, and OH stretching vibrations of water, desirable for characterizing biological tissue. The background signal from tissue autofluorescence and Raman scattering from fused silica in the fiber is also less in this range.

For practical biomedical and diagnostic applications, to identify a possible disease or pathology, it is desirable that Raman spectroscopy can be applied to in vivo tissue, and useful spectra generated as quickly as possible with the maximum amount of information.

SUMMARY OF THE INVENTION

According to a first aspect of the invention there is provided a diagnostic instrument comprising a monochromatic light source, transmission means to transmit light from the light source to an instrument head, collection means to transmit scattered light from the test site, and spectral analysis apparatus to receive light from the collection means, the spectral analysis apparatus comprising a diffraction grating having a first grating element and a second grating element, wherein the first grating element diffracts light within a first spectral range and the second grating element diffracts light within a second spectral range, the spectral analysis apparatus further comprising a light-sensing apparatus, the first grating element arranged to diffract light onto a first area of the light-sensing apparatus and the second grating element arranged to diffract light onto a second area of the light-sensing apparatus.

The transmission means may comprise a transmission optical fiber.

The collection means may comprise a collection optical fiber.

The collection means may comprise a collection filter to exclude light from the monochromatic light source.

The diagnostic instrument may comprise a plurality of collection fibers.

The ends of the collection fibers proximal to the spectral analysis apparatus may be mounted in a curved configuration to correct for image aberration.

The diagnostic instrument may comprise a ball lens mounted at the instrument head to transmit light from the transmission optical fiber to a test site.

The grating elements may each comprise a transmission or reflection grating.

The first spectral range may be from 800 $cm^{-1}$ to 1800 $cm^{-1}$

The second spectral range may be from 2800 $cm^{-1}$ to 3600 $cm^{-1}$.

The diagnostic instrument may further comprise a processing apparatus, the processing apparatus being operable to receive data from the light-sensing apparatus and generate an output.

The processing apparatus may be operable to simultaneously receive data from the first area and generate a first spectrum and receive data from the second area and generate a second spectrum.

Where the light-sensing apparatus comprises a light-sensor array and the data comprises pixel values, The data may be checked for saturation and rejected if saturation is found.

The step of generating a spectrum may comprise binning corresponding pixels.

The step of generating a spectrum may comprise subtracting a background signal from the received data.

The step of generating a spectrum may comprise smoothing the received data.

The step of generating a spectrum may comprise fitting a polynomial curve to the smoothed received data and subtracting the fitted curve from the smoothed received data.

The diagnostic instrument may be operable to check the spectra for contamination and if the spectra are valid, classify the spectra as corresponding to healthy or abnormal tissue and generate an output accordingly.

The diagnostic instrument may comprise a library of stored spectra and be operable to compare the spectra to the stored spectra.

According to a further aspect of the invention there is provided a method of operating a diagnostic instrument, comprising the steps of transmitting light from a monochromatic light source to a test site, collecting scattered light from the test site, and passing collected scattered light to a spectral analysis apparatus, the spectral analysis apparatus comprising a diffraction grating having a first grating element and a second grating element, wherein the first grating element diffracts light within a first spectral range and the second grating element diffracts light within a second spectral range, the spectral analysis apparatus further comprising a light-sensing apparatus, the first grating element arranged to diffract light onto a first area of the light-sensing apparatus and the second grating element arranged to diffract light onto a second area of the light-sensing apparatus.

The method may comprise receiving data from the first area and generating a first spectrum and receiving data from the second area and generating a second spectrum.

The light-sensing apparatus may comprise a light-sensor array and the data may comprise pixel values.

The data may be checked for saturation and rejected if saturation is found.

The step of generating a spectrum may comprise binning corresponding pixels.

The step of generating a spectrum may comprise subtracting a background signal from the received data.

The step of generating a spectrum may comprise smoothing the received data.

The step of generating a spectrum may comprise fitting a polynomial curve to the smoothed received data and subtracting the fitted curve from the smoothed received data.

The method may comprise the steps of checking the spectra for contamination and, if the spectra are valid, classifying the spectra as corresponding to healthy or abnormal tissue and generating an output accordingly.

The method may comprise the steps of providing a library of stored spectra and the checking and classifying steps may comprise comparing the spectra to the stored spectra.

BRIEF DESCRIPTION OF THE DRAWINGS

An embodiment of the invention is described by way of example only with reference to the accompanying drawings, wherein;

FIG. 1 is a diagrammatic illustration of an endoscope embodying the present invention;

FIG. 1a shows a diagrammatic illustration of an instrument head of the endoscope of FIG. 1;

FIG. 1c is a diagrammatic illustration of the spectral analysis apparatus of FIG. 1 on a larger scale;

FIG. 9b is a graph showing the principle component loadings of the graph of FIG. 9a; and FIG. 9c is a plot of the principle component scores of the data of FIG. 9a.

DETAILED DESCRIPTION OF THE PREFERRED EMBODIMENTS

Figure 1B:
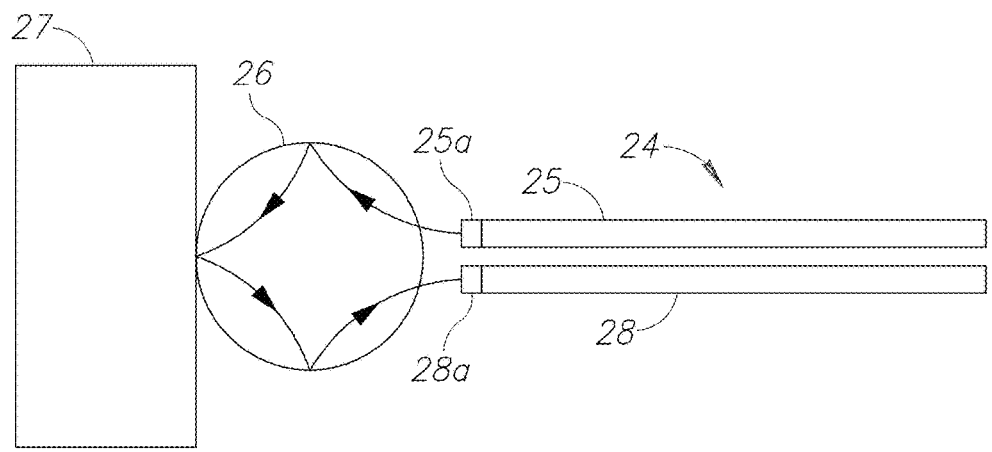
FIG. 1b is a diagrammatic illustration of the ball lens and fiber bundle of FIG. 1a on a larger scale.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before explaining at least one embodiment of the invention in detail, it is to be understood that the invention is not limited in its application to the details of construction and the arrangement of the components set forth in the following description or illustrated n the drawings. The invention is applicable to other embodiments or of being practiced or carried out in various ways. Also, it is to be understood that the phraseology and terminology employed herein is for the purpose of description and should not be regarded as limiting.

Referring now to FIG. 1, a diagnostic instrument comprising an endoscope system generally embodying the invention is shown at 10. The endoscope itself is shown at 11 and an instrument head 12 of the endoscope 11 is generally illustrated in FIG. 1a. To provide for guidance and visual viewing of the area being tested, the endoscope 11 is provided with a suitable video system in general shown at 13. Light from a xenon light source is transmitted to illumination windows 15 in the end of the endoscope 12. CCDs 16 and 17, responsive to white light reflection imaging, narrowband imaging or autofluorescence imaging, receive the reflected light and transmit data to a video processor ("VPU") generally shown at 18. The video information is displayed on a monitor diagrammatically illustrated at 19. The video system 13 allows for visual inspection of the tested tissues and for guidance of the endoscope to a desired position. Processing results can be presented on a suitable display 36.

The Raman spectroscopy apparatus is generally shown at 20. A monochromatic laser source is shown at 21, in the present example a diode laser with an output wavelength of about 785 nm. Light from the laser diode 21 is passed through a proximal band pass filter 22, comprising a narrowband pass filter being centred at 785 nm with a full width half max of ±2.5 nm. The light is passed through a coupling into an excitation optical fiber 25 provided as part of a fiber bundle 24. The excitation fiber 25 has a diameter of 200 µm and a numerical aperture ('NA') 0 f 0.22. A distal band pass filter 25a is located at the instrument head end of the excitation fiber 25, in the present example comprising a coating deposited on the end of the fiber 25. The distal band pass filter 25a has the same band pass characteristics as the proximal band pass filter 22. Light transmitted by the excitation fiber 25 enters a ball lens 26 at the end of the endoscope 11, in the present example comprising a sapphire ball lens with a diameter of about 1.0 mm and a refractive index n=1.77. As illustrated in FIG. 1b, transmitted light from the excitation optical fiber 25 is internally reflected within the ball lens 26. Where the ball lens is in contact with the tissue to be tested, as shown here at 27, the transmitted light from the excitation fiber 25 at least in part undergoes Raman scattering within the tissue 27, to a depth of ~140 μm. The scattered light is again internally reflected in the ball lens 26 and received in a plurality of collection fibers 28, also provided as part of the fiber bundle 24. For clarity, one fiber 28 is shown in FIG. 1, but in the present example twenty-six 100 μm collection fibers are used, with an NA of 0.22. The collection fibres 28 may be arranged in any suitable configuration, for example in a circular arrangement surrounding the excitation fiber 25.

The collection fibers 28 are provided with a distal inline long-pass filter 28a at the instrument head end. In a similar manner to the distal band pass filter 25a, the distal inline long-pass filter 28a is formed as a coating deposited on the end of each collection fiber 28, and has a cut-off at ~800 nm, thus blocking light from the laser source 21 which has not undergone Raman scattering. Collected scattered light returned by collection fibers 28 is passed through a proximal long pass inline collection filter 29 which similarly has a cutoff at ~800 nm. The configuration of sapphire ball lens 26, excitation and collection fibers 25, 28, distal and proximal band-pass filters 22, 25a, and proximal and distal long-pass filters 28a, 29 provides a good system for selectively collecting backscattered Raman photons from the tissue 27.

As illustrated in FIG. 1c, the scattered returned light is then separated at spectrograph 30. Light from the collection fiber 28 is focussed by lens 31 and passed through a curve-configured fiber array and a collimating lens onto a grating 32 comprising a pair of volume holographic phase grating elements 32a, 32b. The grating elements 32a, 32b comprise transmissive diffraction gratings. The diffracted light from grating 32 is focussed by lens 33 onto a light-sensing array 34, in the present example a charge-couple device ('CCD') comprising a 1340×400 pixel array with a pixel spacing of 20×20 microns.

Figure 1D:
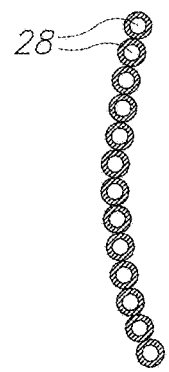
FIG. 1d is an illustration of the configuration of the proximal ends of the collection fibers.

A common problem with transmission-grating spectrographs is that the spectral lines are slightly curved, due to light rays from different parts of the slit arriving at the grating at different angles of incidence. To compensate for this image aberration, the proximal ends of the plurality of collection fibers 28 are mounted in a parabola as shown in FIG. 1d. The curve of the proximal ends of the fibers 28 is selected to be in an equal and opposite sense to the curvature which would be induced in an image of a straight slit. Accordingly, the spectral lines imaged on the CCD by the combination of the parabolically-arranged fiber ends and the grating 32 are straight with no or minimal curvature. By arranging the fibers 28 in this manner, the spectral resolution can be improved as compared to a conventional single-slit imaging spectrograph.

As mentioned above, the grating 32 is a transmission or reflection grating comprising two distinct volume phase holographic grating elements 32a, 32b. The grating elements 32a, 32b are selected such that each grating responds to different spectral ranges. The grating elements 32a, 32b are mounted with a small angular offset, such that the grating 32 disperses the spectra with a small angle onto first and second areas of the light-sensing array 34. For convenience, in this description the direction in which each spectrum are dispersed is referred to as the horizontal direction and the perpendicular direction as being the vertical direction. In the present example the first and second areas are offset in the vertical direction. The spectral range is selected at each grating is selected such that one grating scatters light in a first spectral range, the fingerprint range and the other grating scatters light in a second spectral range, the high wavenumber range. By dispersing the scattered light in each spectral range with a vertical offset in this manner, the Raman spectrum in each wavelength range can be simultaneously read from the light-sensing array 34.

Figure 2:
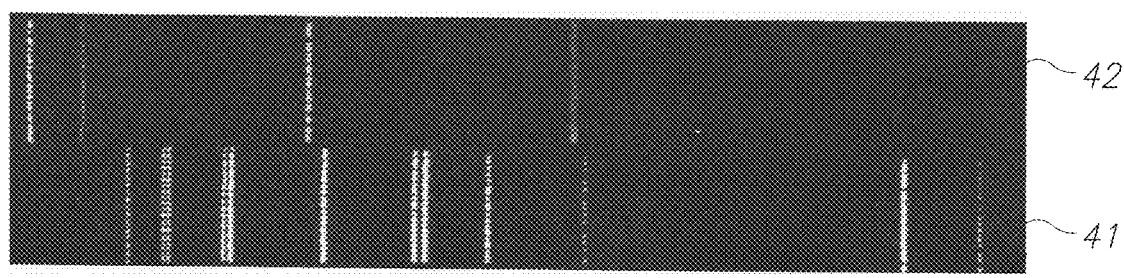
FIG. 2 shows an example image captured by the CCD of FIG. 1 when illuminated by a calibrating argon/mercury light.

As shown in the calibration image of FIG. 2, where the fiber bundle is transmitting light from an argon/mercury lamp with distinct atomic emission lines, the spectral lines in the two wavelength ranges are clearly vertically offset with minimal or no overlap, and are straight and clearly defined in the vertical direction.

Given the pixel spacing and dispersion of the grating elements 32a, 32b, the lower area 41 as shown in FIG. 2 corresponds to the FP region, from 150 to 1950 cm$^{-1}$ with a resolution of 3 cm$^{-1}$, and the upper area 42 corresponds to the spectral range of 1750 to 3600 cm$^{-1}$ which includes a non-specific Raman information region of about 1800 to 2800 cm$^{-1}$ and the HW region, i.e. 2800 to 3600 cm$^{-1}$ with a resolution of 6 cm$^{-1}$.

The image data from the light-sensing array 34 is processed in the following manner, with reference to FIGS. 3 and 4. The spectral data from each region of the image sensing array are treated separately, but each set of data is processed as shown in FIG. 4.

Figure 3:
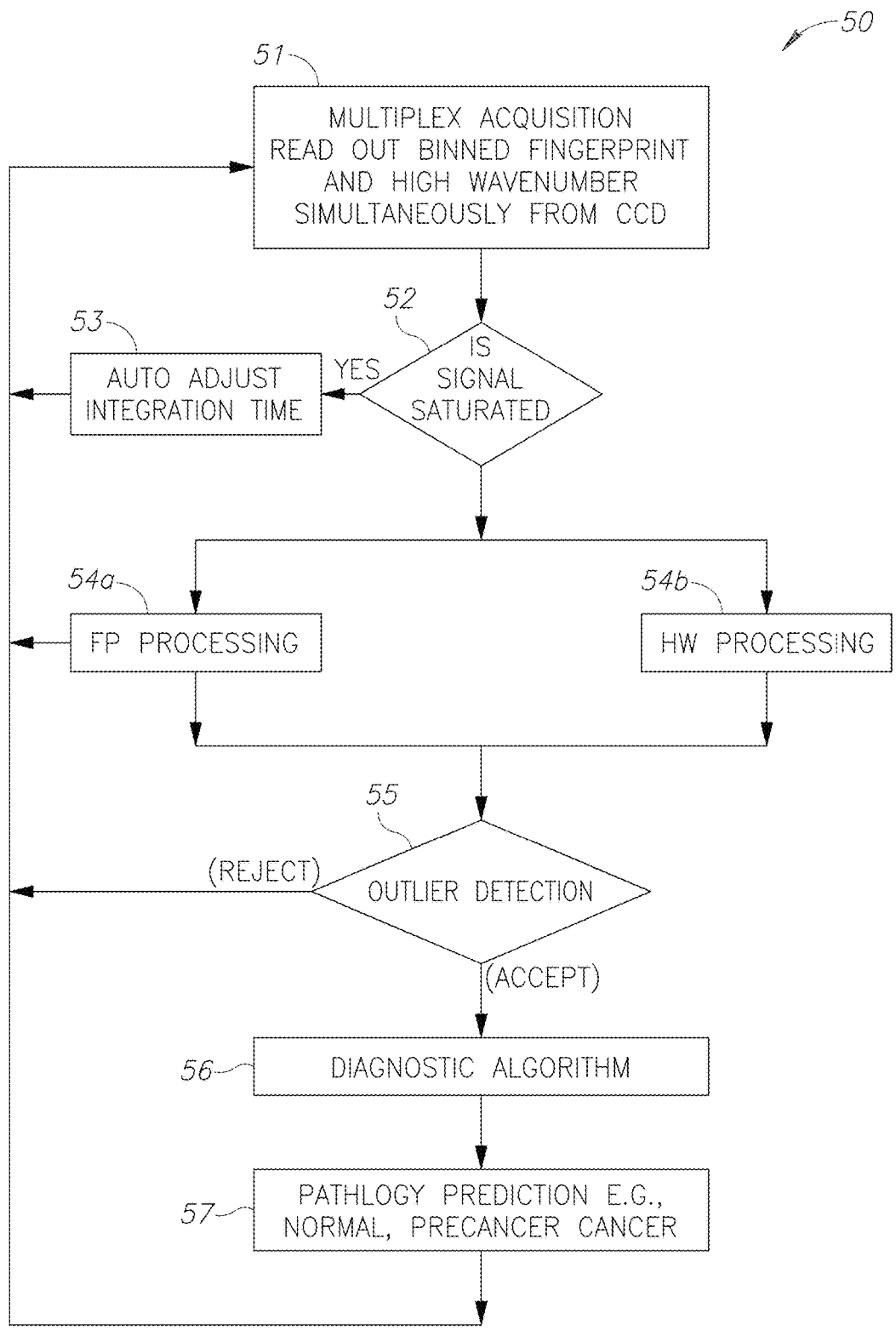
FIG. 3 is a flow diagram showing a method embodying the present invention.
Figure 4:
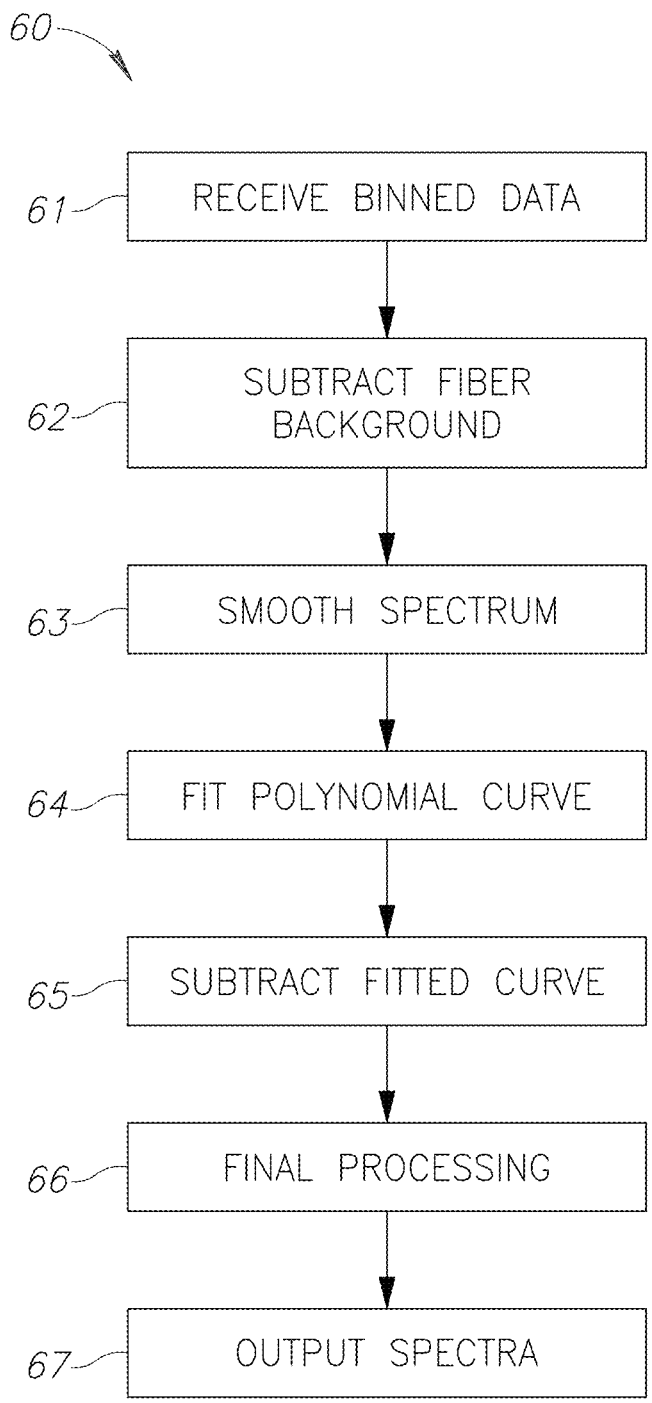
FIG. 4 is a flow diagram, showing part of the method of FIG. 3 in more detail.

The processing method is illustrated at 50 in FIG. 3. At step 51, the pixel values from CCD 34 are read out, and the corresponding vertical pixels within each area 41, 42 are binned, to maximise the signal to noise ratio at each wavelength. It will be apparent that the parabolic arrangement of the collection fibers to reduce or minimise aberration is advantageous at this step, as the corresponding pixels can be binned without having to compensate for line curvature or aberration in software and without loss of resolution.

At 52, the data is checked for saturation, i.e. whether any of the pixel values are at a maximum value. If so, then at step 53 the integration time of the CCD 34 is adjusted and a new image acquired with a shorter integration time which is acquired at step 51.

Figure 5:
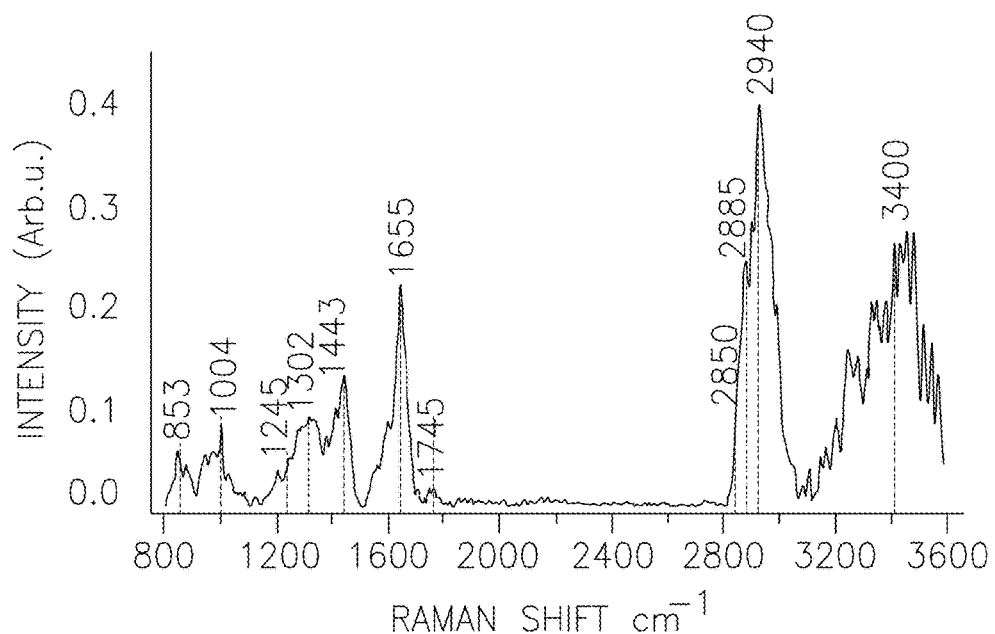
FIG. 5 is an example of a Raman spectrum obtained from a palm of a healthy volunteer using the endoscope of FIG. 1.

If the signal is not saturated, then at step 54a the region 41 corresponding to the FP spectral range is processed. Similarly data from the region 42 corresponding to the HW spectral range is processed at step 54b. Steps 54a, 54b are discussed in more detail below with reference to FIG. 4. Examples of spectra obtained using the method are shown in FIGS. 4 and 5 and discussed in more detail below.

At step 55, outlier detection is performed, to check that the spectra from steps 54a, 54b correspond to a valid signal from tissue and not from contaminants. If the spectra are not valid, the spectra are rejected and new images are acquired at step 51.

In the present example, the outlier detection step is performed using principal component analysis ('PCA') of the captured spectra compared to a database or library of stored spectra, diagrammatically illustrated at 35a. The library of spectra contains spectra from healthy, abnormal and pre-cancerous tissue. PCA is a known method of analysing a data set by characterising the variability of the data set in terms of a smaller number of variables—the principle components—, their relative weights, and an error term for each group of values corresponding to a particular measurement which is a measure of how well the derived principal components match that measurement. In this case PCA is able to reduce the high dimensionality of the library of stored spectra to a smaller number of variables, typically 2 to 5, which forms a model which can be stored for subsequent use. By using the error term, a captured spectrum can be assessed as a genuine spectrum or an outlier. In the present example, the Hotelling $T^2$ and Q-residual statistics are calculated. The Q-residual statistic is an indicator of how good or bad a fit the derived model is to the measured data, while the $T^2$ statistic is a measure of how far the measurement is from the mean or centre of the model.

Figure 7:
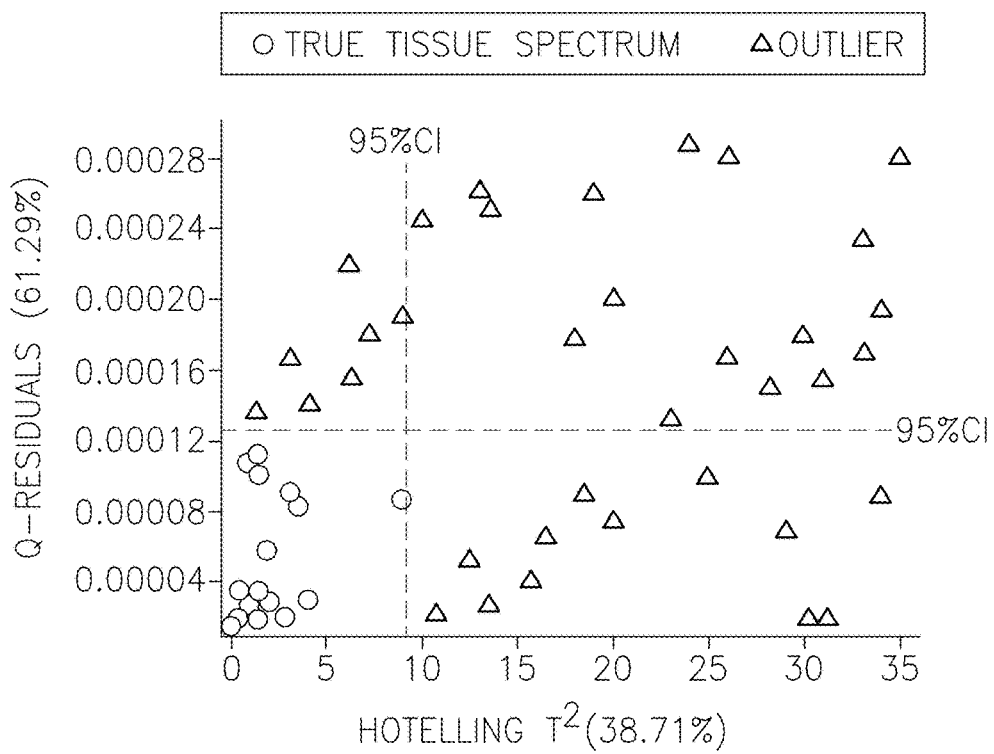
FIG. 7 is a plot of Hotelling $T^2$ and Q-residual statistics for a library of spectra.

When a new spectrum is captured, PCA is performed on the new spectrum and the Hotelling $T^2$ and Q-residual statistics are calculated. Only spectra within the 95% confidence interval of both the $T^2$ and Q-residual statistics of the stored model are accepted. The Hotelling $T^2$ and Q-residual statistics for the library of stored spectra are plotted on the graph of FIG. 7. Spectra in the 95% confidence interval for both statistics are shown in blue in the bottom left-hand corner of the graph. If the Hotelling $T^2$ and Q-residual statistics for measured spectra lie outside this region, they are rejected as outliers. It will be apparent that the library of spectra is selected such that genuine spectra from abnormal tissue are not rejected.

Figure 8:
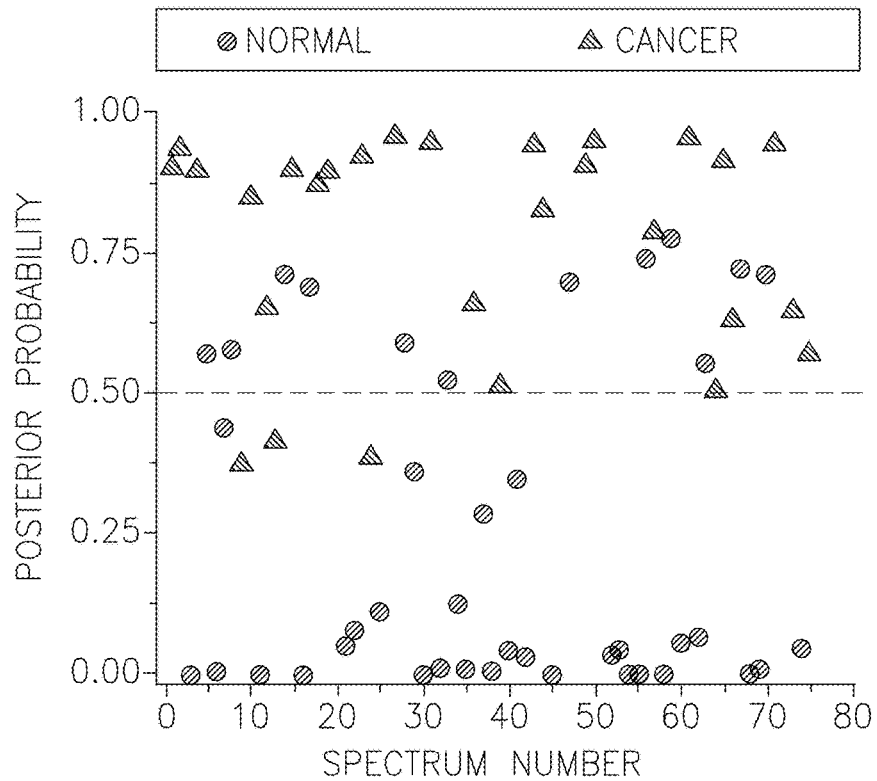
FIG. 8 is a plot of classifications of a plurality of captured spectra.

If the spectra are valid, then at steps 56 further processing steps may be performed, for example to identify spectral characteristics associated with cancerous or precancerous cells, or with other diseases or disorders. In this example, the library of stored spectra may once again be used, as it contains examples of healthy, precancerous and cancerous tissue and may be used in a suitable manner to classify the captured spectra. Alternatively, separate libraries may be used for each step if appropriate or desirable. An example of a suitable technique is probabilistic partial least squares discriminant analysis ('PLS-DA'), in particular because the aim is to classify tissue into one of two states, healthy and abnormal or cancerous. FIG. 8 shows an example set of spectra which have been classified in this manner, with low probabilities indicating healthy tissue and higher probabilities corresponding to cancerous tissue. Any other suitable classification or recognition method may be used at this step.

At step 57, the pathology associated with the results of step 56 and any other desired processing results can be determined, and may be presented on a suitable display 36 or other output such as auditory feedback.

The processing steps 54a, 54b are now discussed in more detail with reference to FIG. 4, the method being illustrated at 60. At step 61 the binned spectra are received and, at step 62, the fiber background is subtracted. This is the spectral component from Raman scattering from fused silica within the optical fiber. The fiber background is stored, or captured prior to the test. This removes that part of the returned signal that does not originate from within the tissue.

At step 63, the spectra are smoothed, by using a suitable averaging window or technique. In the present example, Savitzy-Golay smoothing with a window width of 3 to 5 pixels is used, as this is found to improve the signal quality in noisy Raman spectra.

At step 64, a polynomial curve is fitted to each of the smoothed spectra. The choice of the order of the polynomial curve fitted depends on the spectral range and shape of the background signal resulting from tissue autofluorescence. In the present example, a third- or first-order polynomial is fitted in the HW region and a fifth-order polynomial in the FP region.

At step 65, the fitted curve is subtracted from the corresponding smoothed spectrum. This removes the background signal while leaving the characteristic Raman spectral peaks.

At step 66, other processing steps are performed to improve visualisation and presentation of the spectra. The spectra can for example be normalised, so that there is a given area under each line, or combined to give an apparently continuous spectrum by averaging the overlapping region, or otherwise. At step 67 the spectra are output for use in the diagnostic and pathology steps 56, 57 of FIG. 3.

In the present example, the method is implemented in software on a processing apparatus comprising a personal computer 35, which interfaces with and controls the CCD 34 and laser 21, performs binning and read out of the two areas of the CCD 34 and carries out the analysis of the spectra. It will be apparent that any other processing apparatus with any suitable combination of general purpose or dedicated hardware and software may be used. The database of spectra used in the outlier detection and diagnostic steps is shown diagrammatically at 35a. It will be clear that the database may be stored on the computer 35 or remotely and accessed as needed. The data is processed in real time, in the present example in less than 0.1 s. As the spectra are acquired with an integration time of ~1 s, the system is suitable for use in real time.

Figure 6:
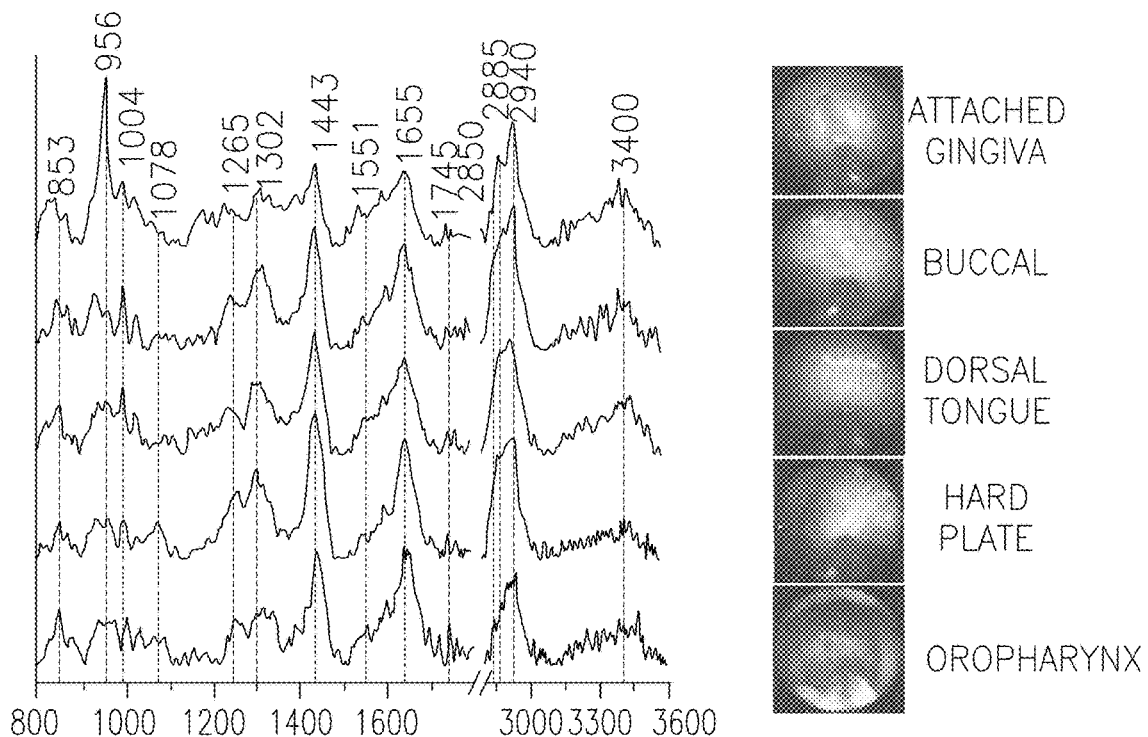
FIG. 6 comprises a plurality of examples of Raman spectra obtained from various tissue types of a healthy volunteer using the endoscope of FIG. 1.

Examples of spectra obtained using an instrument embodying the present invention are shown as FIGS. 5 and 6. FIG. 5 shows the Raman spectra from the palm tissue of a healthy volunteer. The Raman spectrum in the FP region shows narrow Raman peaks near (i.e., 853 cm$^{-1}$ (v(C—C)), 1004 cm$^{-1}$ (vs(C—C)), 1245 cm$^{-1}$ (amide III v(C—N) and δ(N—H) of proteins), 1302 cm$^{-1}$ (CH$_3$CH$_2$ twisting and wagging), 1443 cm$^{-1}$ (δ(CH$_2$) deformation), 1655 cm$^{-1}$ (amide I v(C=O) of proteins) and 1745 cm−1 v(C=O)). On the other hand, broader intense Raman bands are observed in the HW region (i.e., 2850 cm$^{-1}$ and 2885 cm$^{-1}$ (CH$_2$ stretching), 2940 cm$^{-1}$ (CH$_3$ stretching) and 3400 cm$^{-1}$ (OH stretching)). No prominent Raman peaks are present in the in the spectral range (i.e., 1800-2800 cm$^{-1}$).

As an example of the use of an endoscopic system for real-time in vivo tissue Raman measurements of epithelial tissues under wide-field endoscopic imaging, FIG. 6 shows in vivo Raman spectra acquired from different anatomical sites in the head and neck (i.e., attached gingiva, buccal mucosa, dorsal tongue, hard palate and oropharynx) of a healthy volunteer as well as the corresponding wide-field endoscopic images simultaneously acquired from a healthy volunteer undergoing endoscopic examination. The in vivo Raman spectra could be measured with an integration time of 1.0 s and presented on the Raman endoscopy monitor in real-time. Highly resolved Raman peaks are observed in the FP range with tentative molecular assignments near 853 cm$^{-1}$ (v(C—C) proteins), 956 cm$^{-1}$ (vs(P—O) of hydroxyapatite), 1004 cm$^{-1}$ (vs(C—C) ring breathing of phenylalanine), 1078 cm$^{-1}$ (v(C—C) of lipids), 1265 cm$^{-1}$ (amide III v(C—N) and δ(N—H) of proteins), 1302 cm$^{-1}$ (CH$_3$CH$_2$ twisting and wagging of proteins), 1445 cm$^{-1}$ (δ(CH$_2$) deformation of proteins and lipids), 1655 cm$^{-1}$ (amide I v(C=O) of proteins) and 1745 cm$^{-1}$ v(C=O) of lipids. Intense Raman peaks are also seen in the HW region such as 2850 and 2885 cm$^{-1}$ (symmetric and asymmetric CH$_2$ stretching of lipids), 2940 cm$^{-1}$ (CH$_3$ stretching of proteins) as well as the broad Raman band of water (OH stretching vibrations peaking at 3400 cm$^{-1}$ in the 3100-3600 cm$^{-1}$ region).

Figure 9A:
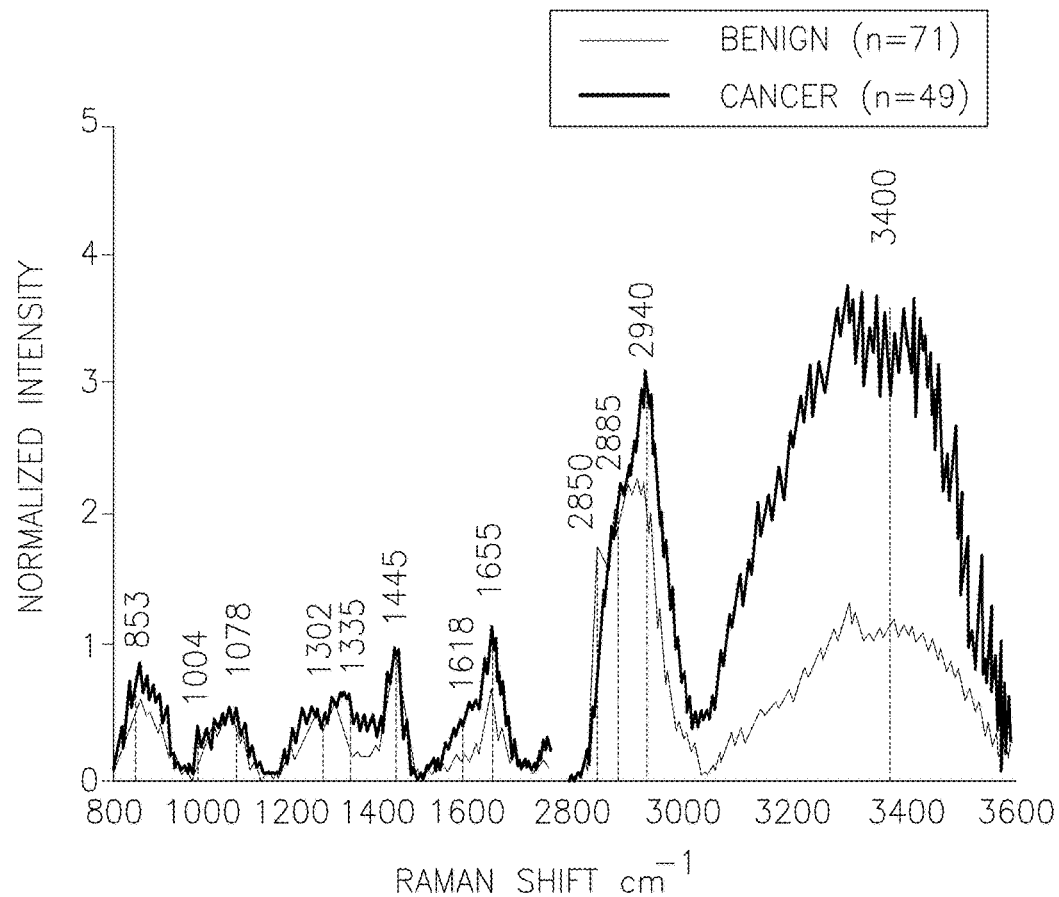
FIG. 9a is a graph showing mean in vivo spectra for healthy and cancerous colon tissue.
Figure 9B:
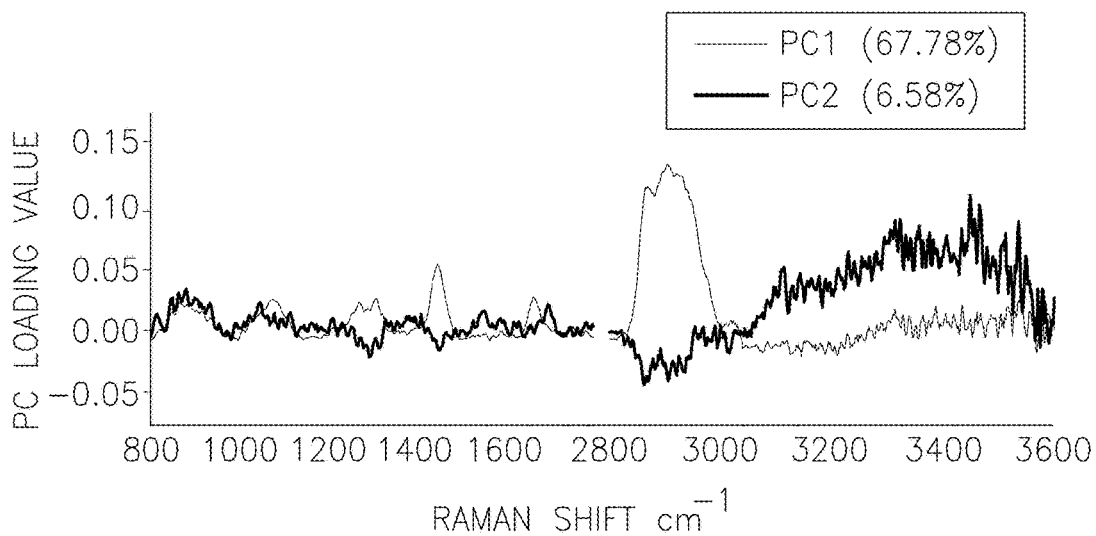
Figure 9C:
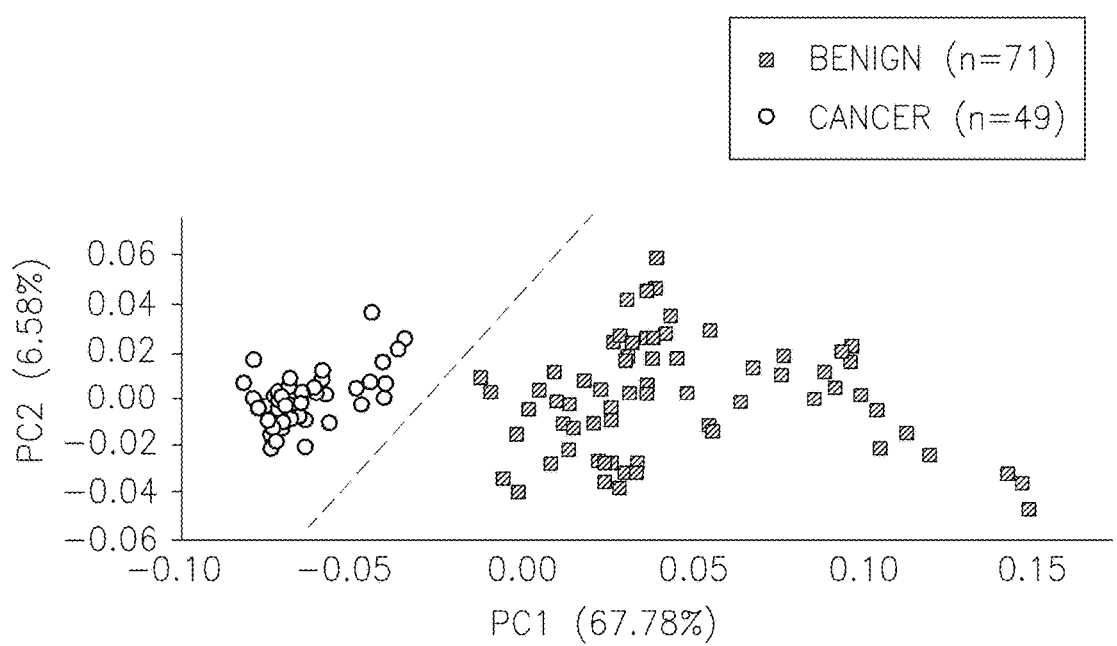

A further example of the use of a an instrument as described herein is the in vivo detection of colon cancer, where high quality Raman spectra of colon tissue were acquired in the FP and HW ranges, from 400 to 3600 cm$^{-1}$ and evaluated in real-time (<0.5 sec) during clinical colonoscopy. FIG. 9a shows the representative mean of in vivo Raman spectra of benign and cancerous colon tissue from four patients, revealing significant changes (p<0.005) in the relative percentage of distinctive biomolecules associated with pathological changes, particularly of C—C stretching of proteins (936 cm$^{-1}$), phenylalanine (1004 cm$^{-1}$), DNA at 1335-1375 cm$^{-1}$, and Amide I of proteins (1655 cm$^{-1}$). Intense Raman peaks are also seen in the HW region such as 2850 and 2885 cm$^{-1}$ (symmetric and asymmetric CH$_2$ stretching of lipids), 2940 cm$^{-1}$ (CH3 stretching of proteins), as well as the broad Raman band of water (OH stretching vibrations that peak at 3400 cm$^{-1}$ in the 3100 to 3600 cm$^{-1}$ region). The complimentary FP and HW Raman molecular fingerprints observed reflect a multitude of endogenous optical biomarkers of colonic (e.g., onco-proteins, DNA content, etc.) including water content/conformation in the cells of the epithelium. The complimentary OH stretching vibrations have been found to be associated with aquaporins and protein/water interactions in cancerous tissues. A principal component analysis (PCA) with two principal components (PCs) loadings as showing in FIG. 9b was employed to evaluate the diagnostic utility. FIG. 9c shows the PC scores (i.e., PC1 vs. PC2) for benign and cancerous tissues. The discrimination line plotted in the PC scatter plot could distinguish colon cancer from benign tissue with sensitivity of 100.0% (49/49) and specificity of 100.0% (71/71) based on the complimentary FP and HW spectral features.

Accordingly, the invention as described herein provides an instrument which allows for high-resolution Raman spectroscopy of in vivo tissue across a wide spectral range, to maximise the scope and quality of information available for tissue diagnosis.

Although the instrument described herein is an endoscope with visualisation or guidance means, it will be apparent that the invention may be implemented in any other instrument or suitable apparatus.

In the above description, an embodiment is an example or implementation of the invention. The various appearances of "one embodiment", "an embodiment" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Furthermore, it is to be understood that the invention can be carried out or practiced in various ways and that the invention can be implemented in embodiments other than the ones outlined in the description above.

Meanings of technical and scientific terms used herein are to be commonly understood as by one of ordinary skill in the art to which the invention belong, unless otherwise defined.

The invention claimed is:

1. A real-time diagnostic instrument comprising;
a monochromatic light source;
an instrument head;
transmission means to transmit light from the light source to the instrument head;
collection means to transmit scattered light; and
spectral analysis apparatus to receive light from the collection means,
the spectral analysis apparatus comprising a diffraction grating having a first grating element and a second grating element, wherein the first grating element diffracts light within a first spectral range of 800 cm$^{-1}$ to 1800 cm$^{-1}$ and the second grating element diffracts light within a distinct second spectral range of 2800 cm$^{-1}$ to 3600 cm$^{-1}$,
the spectral analysis apparatus further comprising a light-sensing apparatus,
wherein the first grating element is arranged to diffract light onto a first area of the light-sensing apparatus and the second grating element arranged to diffract light onto a second area of the light-sensing apparatus;
a processing apparatus, the processing apparatus being operable to receive data from the spectral analysis apparatus and generate an output, wherein the processing apparatus is operable to simultaneously receive data from the first area and generate a first spectrum and receive data from the second area and generate a second spectrum; and
a library of stored spectra and operable to compare the spectra to the stored spectra in real-time, wherein the processing apparatus is operable to check the spectra for contamination and classify the spectra as corresponding to healthy or abnormal tissue.

2. The real-time diagnostic instrument according to claim 1 wherein the transmission means comprises a transmission optical fiber, and the collection means comprises a collection optical fiber having a proximal end and a collection filter to exclude light from the monochromatic light source.

3. The real-time diagnostic instrument according to claim 2 wherein the collection means comprises a plurality of collection fibers and ends of the collection fibers proximal to the spectral analysis apparatus are mounted in a curved configuration to correct for image aberration.

4. The real-time diagnostic instrument according to claim 2 further comprising a ball lens to transmit light from the transmission optical fiber to a test site.

5. The real-time diagnostic instrument according to claim 1 further comprising a processing apparatus operable to simultaneously receive data from the first area and generate a first spectrum and receive data from the second area and generate a second spectrum.

6. A method of operating a diagnostic instrument in real-time, comprising:
transmitting light from a monochromatic light source to a test site;
collecting scattered light from the test site;
passing collected scattered light to a spectral analysis apparatus comprising:
a diffraction grating having a first grating element and a second grating element; and
a light-sensing apparatus;
simultaneously diffracting light within a first spectral range of 800 cm$^{-1}$ to 1800 cm$^{-1}$ with the first grating element onto a first area of the light sensing apparatus and diffracting light within a distinct second spectral range of 2800 cm$^{-1}$ to 3600 cm$^{-1}$ with the second grating element onto a second area of the light sensing apparatus;
receiving data from the first area and generating a first spectrum and receiving data from the second area and generating a second spectrum;
classifying the spectra as corresponding to healthy or abnormal tissue and generating an output accordingly for valid spectra; and
providing a library of stored spectra and wherein the checking and classifying steps comprise comparing the spectra to the stored spectra in real-time.

7. The method according to claim 6 further comprising receiving data from the first area and generating a first spectrum and receiving data from the second area and generating a second spectrum.

8. The method according to claim 7 further comprising checking the received data for saturation.

\* \* \* \* \*